United States Patent [19]

Ogawa et al.

[11] Patent Number: 4,582,868

[45] Date of Patent: Apr. 15, 1986

[54] MEDIUM FOR ELECTROPHORESIS

[75] Inventors: Masashi Ogawa, Asaka; Taku Nakamura, Minami-ashigara, both of Japan

[73] Assignee: Fuji Photo Film Co., Ltd., Kanagawa, Japan

[21] Appl. No.: 590,724

[22] Filed: Mar. 19, 1984

[30] Foreign Application Priority Data

Mar. 18, 1983 [JP] Japan .................................. 58-45548

[51] Int. Cl.$^4$ ............................................... C08K 5/21
[52] U.S. Cl. ................................ 524/211; 204/182.8; 524/27; 524/56; 524/233; 524/502; 524/503; 524/515; 524/516; 524/521
[58] Field of Search .................. 204/180 G; 524/211, 524/233, 515, 516, 521, 502, 503, 27, 56

[56] References Cited

U.S. PATENT DOCUMENTS 4,201,587  5/1980  Bedell et al. ........................ 430/536
4,415,428  11/1983  Nochumson et al. .......... 204/299 R

FOREIGN PATENT DOCUMENTS 0119090  9/1984  European Pat. Off. .
0119808  9/1984  European Pat. Off. .
0126639  11/1984  European Pat. Off. .

OTHER PUBLICATIONS

Chemical Abstracts; Taroritzky, Peter, "Composition for the Preparation of Improved Acrylamide and Acrylic Acid Polymers Containing a 1,3-Dione", May 8, 1981, vol. 96, 1982.
Chemical Abstracts, Yasuo Ogawa, "Acrylamide Polymer Powders", Feb. 23, 1977, vol. 86, 1977.

*Primary Examiner*—Joseph L. Schofer
*Assistant Examiner*—J. M. Reddick
*Attorney, Agent, or Firm*—Toren, McGeady, Stanger, Goldberg & Kiel

[57] ABSTRACT

A medium for electrophoresis in the form of an aqueous gel comprising an acrylamide copolymer having at least one specifically selected repeating unit; and a compound containing at least one carbamoyl group such as urea or formamide which serves as modifier.

6 Claims, No Drawings

MEDIUM FOR ELECTROPHORESIS

BACKGROUND OF THE INVENTION

1. Field of the Invention

This invention relates to a medium for electrophoresis, and more particularly relates to a medium for electrophoresis suitably employable for determination of base sequence of DNA, RNA, their fragment, and their derivatives.

2. Description of Prior Arts

In the method for determination of the base sequence of DNA, RNA, their fragments, and their derivatives according to the post-label method, the operation of slab electrophoresis using a polyacrylamide gel membrane (medium) has become essential. Since the study in the genetic engineering technology has greatly advanced recently, quick determination of the base sequence of DNA, etc. is highly desired.

The polyacrylamide gel membrane employable for the above purpose can be prepared by crosslinking polymerization of a monomer such as acrylamide and a two-functional crosslinking agent such as N,N'-methylenebisacrylamide under an oxygen-free condition in the presence of water and a polymerization catalyst. In the course of the preparation of the polyacrylamide gel membrane, a modifier such as urea or formamide is generally incorporated into the membrane.

Since the polymerization reaction for the preparation of polyacrylamide is a radical crosslinking polymerization as described above, the polymerization can be easily inhibited by the presence of oxygen. Therefore, the gel membrane should be prepared in the absence of oxygen. For this reason, a polyacrylamide gel membrane is generally prepared by a process involving: introducing an aqueous solution (gel-forming solution or gel solution) containing acrylamide, a crosslinking agent and a polymerization catalyst into a cell formed between two glass plates with a certain clearance (e.g., 0.3-1 mm); sealing the gel-forming solution from oxygen; and causing the crosslinking polymerization to prepare the desired gel membrane.

The cell employed for the preparation of the gel membrane generally has length of approx. 40 to 100 cm. Accordingly, the introduction of the gel-forming solution into the such a long cell requires careful operation to prevent the solution from foaming. However, if a long period of time is employed for the introduction of the gel-forming solution into the cell, the gelation advances prior to completion of the introduction, whereby failing to prepare a polyacrylamide gel membrane of the desired length. Thus, the preparation of a polyacrylamide gel having the desired length requires highly skilled operation, as well as the operation keeping the solution from oxygen. This is one reason to make it difficult to prepare the polyacrylamide gel membrane (medium) in a mass scale.

SUMMARY OF THE INVENTION

An object of the present invention is to provide a medium for electrophoresis in the form of an aqueous gel which can be prepared in the presence of oxygen.

There is provided by the present invention a medium for electrophoresis in the form of an aqueous gel comprising an acrylamide copolymer having at least one repeating unit selected from the group consisting of:

(1) a repeating unit having the formula (1):

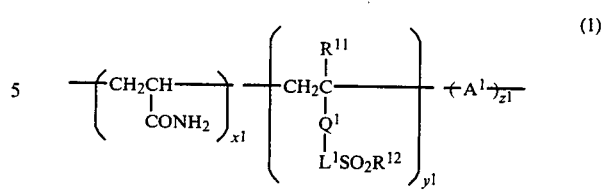

in which $R^{11}$ is the hydrogen atom or an alkyl group containing 1-6 carbon atoms; $Q^1$ is $-COO-$, $-CON(R^{11})-$, or an arylene group containing 6-10 carbon atoms; $L^1$ is a divalent group containing at least one linkage selected from the group consisting of $-COO-$ and $-CON(R^{11})-$ and containing 3-15 carbon atoms, or a divalent group containing at least one linkage selected from the group consisting of $-O-$, $-N(R^{11})-$, $-CO-$, $-SO-$, $-SO_2-$, $-SO_3-$, $-SO_2N(R^{11})-$, $-N(R^{11})CON(R^{11})-$ and $-N(R^{11})COO-$, and containing 1-12 carbon atoms, in which $R^{11}$ has the same meaning as defined above; $R^{12}$ is $-CH=CH_2$ or $-CH_2CH_2X^1$, in which $X^1$ is a substituent replaceable with a nucleophilic group or releasable in the form of $HX^1$ by a base; $A^1$ is a divalent group derived from an ethylenic unsaturated monomer copolymerizable with monomers forming other unit portions; and $x^1$ and $y^1$ both representing molar percents ranging from 50 to 99, and from 1 to 50, respectively, and $z^1$ represents the remaining molar percent including 0;

(2) a repeating unit having the formula (2):

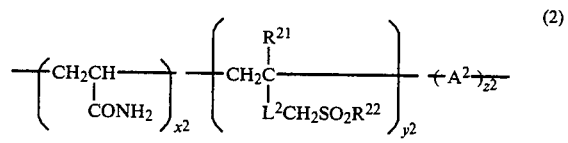

in which $R^{21}$ is the hydrogen atom or an alkyl group containing 1-6 carbon atoms; $R^{22}$ is $-CH=CH_2$ or $-CH_2CH_2X^2$, in which $X^2$ is a substituent replaceable with a nucleophilic group or releasable in the form of $HX^2$ by a base; $L^2$ is a divalent group selected from the group consisting of an alkylene group containing 1-6 carbon atoms, an arylene group containing 6-12 carbon atoms, $-COZ^2-$, and $-COZ^2R^{23}-$, in which $R^{23}$ is an alkylene group containing 1-6 carbon atoms, or an arylene group containing 6-12 carbon atoms, and $Z^2$ is the oxygen atom or NH; $A^2$ is a divalent group derived from an ethylenic unsaturated monomer copolymerizable with monomers forming other unit portions; and $x^2$ and $y^2$ both representing molar percents range from 50 to 99, and from 1 to 50, respectively, and $z^2$ represents the remaining molar percent including 0; and (3) a repeating unit having the formula (3):

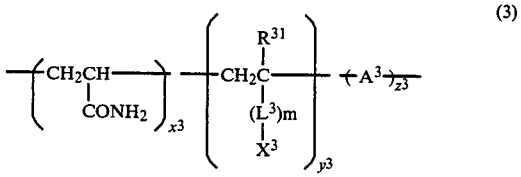

in which $R^{31}$ is the hydrogen atom or an alkyl group containing 1-6 carbon atoms; $L^3$ is a divalent linkage group containing 1-20 carbon atoms; $X^3$ is an active ester; $A^3$ is a divalent group derived from an ethylenic unsaturated monomer copolymerizable with monomers forming other unit portions; $x^3$ and $y^3$ both representing molar percents range from 50 to 99, and from 1 to 50, respectively, and $z^3$ represents the remaining molar percent including 0; and m is 0 or 1; and a compound containing at least one carbamoyl group serving as modifier.

DETAILED DESCRIPTION OF THE INVENTION

The medium electrophoresis in the form of an aqueous gel according to the present invention comprises an acrylamide copolymer having at least one repeating unit selected from the group consisting of the following repeating units (1), (2) and (3). Particularly preferred is a polymer represented by the repeating unit (1).

(1) A repeating unit having the formula (1):

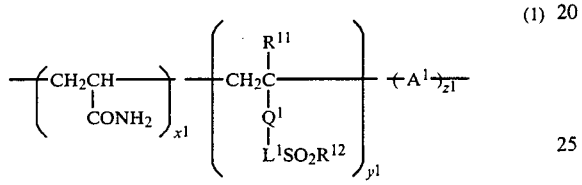

in which $R^{11}$ is the hydrogen atom or an alkyl group containing 1-6 carbon atoms; $Q^1$ is —COO—, —CON($R^{11}$)—, or an arylene group containing 6-10 carbon atoms; $L^1$ is a divalent group containing at least one linkage selected from the group consisting of —COO— and —CON($R^{11}$)— and containing 3-15 carbon atoms, or a divalent group containing at least one linkage selected from the group consisting of —O—, —N($R^{11}$)—, —CO—, —SO—, —SO$_2$—, —SO$_3$—, —SO$_2$N($R^{11}$)—, —N($R^{11}$)CON($R^{11}$)— and —N($R^{11}$)COO—, and containing 1-12 carbon atoms, in which $R^{11}$ has the same meaning as defined above; $R^{12}$ is —CH=CH$_2$ or —CH$_2$CH$_2$X$^1$, in which X$^1$ is a substituent replaceable with a nucleophilic group or releasable in the form of HX$^1$ by a base; $A^1$ is a divalent group derived from an ethylenic unsaturated monomer copolymerizable with monomers forming other unit portions (shown in the left therefrom); and $x^1$ and $y^1$ both representing molar percents range from 50 to 99, and from 1 to 50, respectively, and $z^1$ represents the remaining molar percent including 0;

Examples of $R^{11}$ in the above formula (1) include methyl, ethyl, butyl and n-hexyl groups.

Examples of $Q^1$ include —COO—, —CONH—, —CON(CH$_3$)—, —CON(C$_2$H$_5$)—, —CON(n-C$_4$H$_9$)—,

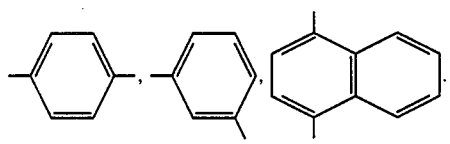

Examples of $L^1$ include the following divalent groups, which can be arranged in any direction within the formula (1), so far as it can connect $Q^1$ and SO$_2$:
—CH$_2$COOCH$_2$, —CH$_2$COOCH$_2$CH$_2$—, —CH$_2$CH$_2$COOCH$_2$—, —(CH$_2$)$_5$COOCH$_2$CH$_2$—, —(CH$_2$)$_{10}$COOCH$_2$CH$_2$—, —CH$_2$NHCOCH$_2$, —CH$_2$NHCOCH$_2$CH$_2$—, —(CH$_2$)$_3$NHCOCH$_2$CH$_2$—, —(CH$_2$)$_5$NHCOCH$_2$CH$_2$—, —(CH$_2$)$_{10}$NHCOCH$_2$CH$_2$—, —CH$_2$OCH$_2$—, —CH$_2$CH$_2$OCH$_2$CH$_2$CH$_2$—, —N(CH$_3$)CH$_2$CH$_2$—, —CH$_2$N(CH$_3$)CH$_2$CH$_2$— —COCH$_2$CH$_2$—, —CH$_2$COCH$_2$CH$_2$—,

—SOCH$_2$CH$_2$—, —CH$_2$SOCH$_2$CH$_2$—, —SO$_2$CH$_2$CH$_2$—, —SO$_2$CH$_2$CH$_2$SO$_2$CH$_2$CH$_2$—, —SO$_2$CH$_2$CH$_2$SO$_2$CH$_2$CH(OH)CH$_2$—, —SO$_3$CH$_2$CH$_2$CH$_2$—, —SO$_3$CH$_2$COOCH$_2$CH$_2$—, —SO$_3$CH$_2$CH$_2$COOCH$_2$CH$_2$—, —SO$_3$CH$_2$CH$_2$CH$_2$—, —SO$_2$NHCH$_2$COOCH$_2$CH$_2$—, —SO$_2$NHCH$_2$CH$_2$COOCH$_2$CH$_2$—, —NHCONHCH$_2$CH$_2$—, —CH$_2$NHCONHCH$_2$CH$_2$—, —NHCOOCH$_2$CH$_2$—, and —CH$_2$NHCOOCH$_2$CH$_2$—.

$R^{12}$ is —CH=CH$_2$ or —CH$_2$CH$_2$X$^1$. Examples of X$^1$ include:
halogen atoms such as chlorine and bromine;
hydroxyl group;
alkylsulfonyloxy groups such as methylsulfonyloxy (H$_3$CSO$_3$—), ethylsulfonyloxy, and propylsulfonyloxy;
arylsulfonyloxy groups such as phenylsulfonyloxy

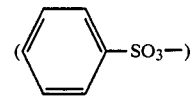

and p-tolylsulfonyloxy; and
alkylcarbonyloxy groups such as acetoxy, propionyloxy, trifluoromethylcarbonyloxy and dichloromethylcarbonyloxy. Accordingly, examples of $R^{12}$ include the following groups:
—CH=CH$_2$, —CH$_2$CH$_2$Cl, —CH$_2$CH$_2$Br, —CH$_2$CH$_2$O$_3$SCH$_3$,

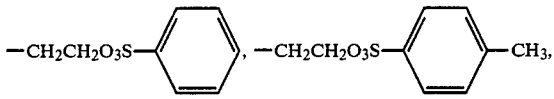

—CH$_2$CH$_2$OH, —CH$_2$CH$_2$OOCCH$_3$, —CH$_2$CH$_2$OOCCF$_3$, and —CH$_2$CH$_2$OOCCHCl$_2$.

Examples of the divalent group represented by $A^1$ include groups derived from the following ethylenic unsaturated monomers: ethylene, propylene, 1-butene, isobutene, styrene, chloromethylstyrene, hydroxymethylstyrene, sodium vinylbenzenesulfonate, sodium vinylbenzylsulfonate, N,N,N-trimethyl-n-vinylbenzylammonium chloride, N,N-dimethyl-N-benzyl-N-vinylbenzylammonium chloride, α-methylstyrene, vinyltoluene, 4-vinylpyridine, 2-vinylpyridine, benzylvinylpyridinium chloride, N-vinylacetamide, N-vinylpyrrolidone, 1-vinyl-2-methylimidazole, mono-ethylenic unsaturated esters of aliphatic carboxylic acid (e.g., vinyl acetate and allyl acetate), ethylenic unsaturated monocarboxylic acids or dicarboxylic acids and salts thereof (e.g., acrylic acid, methacylic acid, itaconic acid, maleic acid, sodium acrylate, potassium acrylate, sodium methacrylate), maleic anhydride, esters of ethylenic unsaturated monocarboxylic acids or dicarboxylic acids (e.g., n-butyl acrylate, n-hexyl acrylate, hydroxyethyl acrylate, cyanoethyl acrylate, (diethylamino)ethyl acrylate, methyl methacrylate, n-butyl methacrylate, benzyl methacrylate, hydroxyethyl methacrylate, chloroethyl methacrylate, methoxyethyl methacrylate, (diethylamino)ethyl methacrylate, N,N,N-triethyl-N-methacryloyloxyethylammonium p-toluenesulfonate, N,N-diethyl-N-methyl-N-methacryloyloxyethylammonium p-toluenesulfonate, dimethyl itaconate, and monobenzyl maleate), amides of ethylenic unsaturated monocarboxylic acid or dicarboxylic acid (e.g., N,N-dimethylacrylamide, N-methylolacrylamide, and N-[(dimethylamino)propyl]acrylamide), N,N,N-trimethyl-N-(acryloylpropyl)ammonium p-toluenesulfonate, sodium 2-acrylamide-2-methylpropanesulfonate, acryloylmorpholine, methacrylamide, N,N-dimethyl-N'-acryloylpropanediamine propionate betaine, and N,N-dimethyl-N'-methacryloylpropanediamine acetate betaine.

In the case that the acrylamide copolymer of the invention is employed in the form of a crosslinked latex, $A^1$ can be other groups derived monomers containing at least two copolymerizable ethylenic unsaturated groups (e.g., divinyl benzene, methylenebisacrylamide, ethyleneglycol diacrylate, trimethylene glycol diacrylate, ethyleneglycol dimethacrylate, trimethylene glycol dimethacrylate, neopentylglycol dimethacrylate, etc.).

(2) A repeating unit having the formula (2):

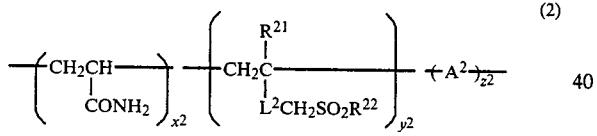

(2)

in which $R^{21}$ is the hydrogen atom or an alkyl group containing 1-6 carbon atoms; $R^{22}$ is $-CH=CH_2$ or $-CH_2CH_2X^2$, in which $X^2$ is a substituent replaceable with a nucleophilic group or releasable in the form of $HX^2$ by a base; $L^2$ is a divalent group selected from the group consisting of an alkylene group containing 1-6 carbon atoms (e.g., methylene, ethylene, and isobutylene), an arylene group containing 6-12 carbon atoms (e.g., phenylene, tolylene, and naphthalene), $-COZ^2-$, and $-COZ^2R^{23}-$, in which $R^{23}$ is an alkylene group containing 1-6 carbon atoms, or an arylene group containing 6-12 carbon atoms, and $Z^2$ is the oxygen atom or NH; $A^2$ is a divalent group derived from an ethylenic unsaturated monomer copolymerizable with monomers forming other unit portions; and $x^2$ and $y^2$ both representing molar percents range from 50 to 99, and from 1 to 50, respectively, and $z^2$ represents the remaining molar percent including 0.

In the formula (2), examples of $R^{21}$, $R^{22}$ and $A^2$ include the respective groups listed for $R^{11}$, $R^{12}$ and $A^1$ of the formula (1).

(3) A repeating unit having the formula (3):

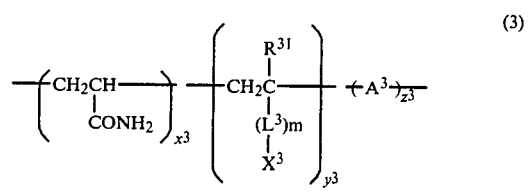

(3)

in which $R^{31}$ is the hydrogen atom or an alkyl group containing 1-6 carbon atoms; $L^3$ is a divalent linkage group containing 1-20 carbon atoms; $X^3$ is an active ester; $A^3$ is a divalent group derived from an ethylenic unsaturated monomer copolymerizable with monomers forming other unit portions; $x^3$ and $y^3$ both representing molar percents range from 50 to 99, and from 1 to 50, respectively, and $z^3$ represents the remaining molar percent including 0; and m is 0 or 1.

In the formula (3), examples of $R^{31}$ and $A^3$ include the groups listed for $R^{11}$ and $A^1$ of the formula (1).

Examples of $L^3$ include the following groups:
$-COCH_2-$, $-COCH_2CH_2OCOCH_2CH_2-$,
$-CONHCH_2-$, $-CONHCH_2CH_2-$,
$-CONHCH_2CH_2CH_2-$, $-CONHCH_2CH_2CH_2CH_2-$, $-CONHCH_2CONHCH_2-$, $-COHCH_2CONHCH_2CONHCH_2-$, $-CONHCH_2NHCOCH_2CH_2CH_2SCH_2CH_2-$, and $-CONHCH_2OCOCH_2CH_2-$.

Examples of $X^3$ include the following groups:

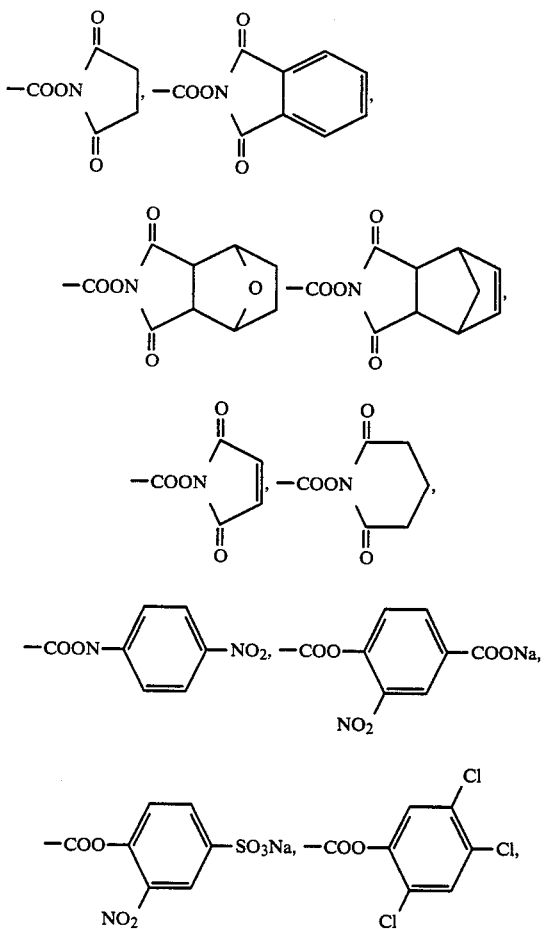

-continued

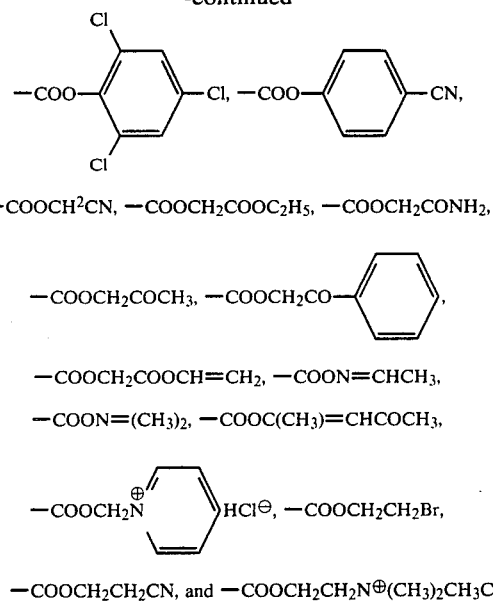

—COOCH²CN, —COOCH₂COOC₂H₅, —COOCH₂CONH₂,

—COOCH₂COCH₃, —COOCH₂CO—,

—COOCH₂COOCH═CH₂, —COON═CHCH₃,

—COON═(CH₃)₂, —COOC(CH₃)═CHCOCH₃,

—COOCH₂NHCl⊖, —COOCH₂CH₂Br,

—COOCH₂CH₂CN, and —COOCH₂CH₂N⊕(CH₃)₂CH₃Cl⊖.

Processes for syntheses of representative ethylenic unsaturated monomers containing a vinylsulfonyl groups or a functional group convertible into a vinylsulfonyl group which are employable for the preparation of the polymers comprising the repeating unit represented by the formula (1), (2) or (3) are illustrated below.

SYNTHESIS EXAMPLE 1

Synthesis of 2-[3-(2-chloroethylsulfonyl)propionyloxy]ethyl acrylate

CH₂═CHCOOCH₂CH₂OCOCH₂CH₂SO₂CH₂CH₂Cl

Into a mixture of 600 ml. of tetrahydrofuran, 45.8 g. of hydroxyethyl acrylate, and 72 g. of 3-(2-chloroethylsulfonyl)propionyl chloride placed in a reaction vessel chilled with ice-water to maintain the temperature below 5° C., a solution of 31.2 g. of pyridine in 100 ml. of tetrahydrofuran was poured dropwise for 1.75 hours. The resulting mixture was stirred at room temperature for 2 hours, and poured into 2.5 l. of ice-water. The aqueous mixture was then extracted with 4 portions of 300 ml. of chloroform. The organic extract was dried over sodium sulfate, and concentrated to give 87 g. of 2-[3-(2-chloroethylsulfonyl)propionyloxy]ethyl acrylate (yield 88%).

SYNTHESIS EXAMPLE 2

Synthesis of N-[3-(2-chloroethylsulfonyl)propanamidomethyl]acrylamide

CH₂═CHCONHCH₂NHCOCH₂CH₂SO₂CH₂CH₂Cl

In a 2-l. reaction vessel, 1,400 ml. of distilled water, 244 g. of sodium sulfite and 220 g. of sodium hydrogencarbonate were stirred to give a solution. To the resulting solution chilled with ice-water to maintain the temperature at approx. 5° C. was dropwise added for 1.5 hours 260 g. of chloroethanesulfonyl chloride. To the resulting mixture was further added dropwise for approx. 15 min. 160 g. of 49% sulfuric acid. The mixture was then stirred at 5° C. for 1 hour, and the produced crystalline precipitate was filtered off. The precipitate was then washed with 400 ml. of distilled water. The filtrate and the water collected from the washing were together introduced into a 3-l. reaction vessel. Into the reaction vessel chilled with ice to maintain the temperature at approx. 5° C. was dropwise added for 30 min. a solution of 246 g. of methylenebisacrylamide in a mixture of 480 ml. of distilled water and 1,480 ml of ethanol. The reaction vessel was then stored in a refrigerator for 5 days to complete the reaction. The precipitated crystals were collected by filtration and washed with 800 ml. of chilled distilled water. The crystals were then recrystallized from 2,000 ml. of 50% aqueous ethanol to give 219 g. of the desired monomer: yield 49%. Analysis: H 5.17%; C 37.90%; N 9.48%; Cl 12.58%.

SYNTHESIS EXAMPLE 3

Synthesis of {[3-(2-chloroethylsulfonyl)propanamido]methyl}styrene

Into a mixture of 100 ml. of tetrahydrofuran, 20.1 g. of vinylbenzylamine, 16.7 g. of triethylamine, and 0.1 g. of hydroquinone placed in a reaction vessel chilled with ice-water a solution of 36.1 g. of β-chloroethylsulfonylpropionyl chloride in 200 ml. of tetrahydrofuran was poured dropwise for 30 min. The resulting mixture was allowed to stand overnight at room temperature. Subsequently, the mixture was poured into a diluted sulfuric acid prepared from 16.5 g. of conc. sulfuric acid and 1.5 l. of ice-water. The produced precipitate was collected by filtration. The collected precipitate was recrystallized from a mixture of 200 ml. of ethanol and 200 ml. of water to give 26.8 g. of {[3-(2-chloroethylsulfonyl)propanamido]methyl}styrene: yield 57%. Analysis: H 5.74%; C 53.47%; N 4.83%; Cl 10.99%; S 10.49%.

SYNTHESIS EXAMPLE 4

Synthesis of 1-[2-(4-vinylphenylsulfonyl)ethylsulfonyl]-3-(2-chloroethyl)sulfonyl-2-propanol

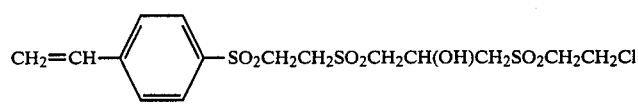

To a mixture of 157 g. of 1,3-bis(2-chloroethyl)sulfonyl-2-propanol (prepared by the method disclosed in Japanese Patent Provisional Publication No. 53(1978)-57257), 1 l. of methanol and 1 l. of distilled water placed in a reaction vessel and heated to 46° C. was dropwise added for 1 hour a solution of 52 g. of potassium vinylbenzenesulfinate in a mixture of 100 ml. of methanol and 100 ml. of distilled water. The resulting mixture was further stirred at 46° C. for 5.5 hours. The produced precipitate was collected to give 55 g. of 1-[2-(4-vinylphenylsulfonyl)ethylsulfonyl]-3-(2-chloroethyl)sulfonyl-2-propanol: yield 49%. Analysis: H 4.67%; C 39.89%; S 21.43%.

Among the polymers defined hereinbefore, polymers comprising the following repeating unit are preferred for the polymer employed for the formation of the adhesive layer according to the present invention.

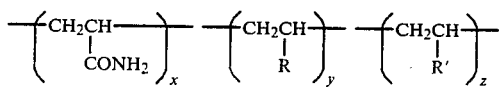

In the above formula, x, y and z mean molar percents for respective groups, and R and R' means the following substituents.

crosslinking reaction of the constituent monomers of the desired copolymers in the presence of water. A crosslinking agent is preferably employed for performing the crosslinking reaction.

The crosslinking agent for obtaining the aqueous acrylamide copolymer gel can be a compound containing in one molecule at least two nucleophilic groups (e.g., amino groups, phenolic hydroxyl groups, sulfinic acid groups, thiol groups, and a combination of amino group and thiol group).

Examples of the crosslinking agent containing the amino groups include ethylenediamine, 1,3-propanediamine, 1,5-pentanediamine, hexamethylenediamine, diethylenetriamine, triethylenetetramine, propylenediamine, di(aminomethyl)ether, 1,4-diamino-2-butene, 1,8-diamino-4-(aminomethyl)octane, xylylenediamine, phenylenediamine, polylysine, polyethylene imine, and gelatin.

| | | |
|---|---|---|
| P-1 | x = 92, y = 8, z = 0, | R = $-COOCH_2CH_2OCOCH_2CH_2SO_2CH=CH_2$ |
| P-2 | x = 92, y = 8, z = 0, | R = $-CONHCH_2NHCOCH_2CH_2SO_2CH=CH_2$ |
| P-3 | x = 80, y = 8, z = 12, | R = $-CONHCH_2NHCOCH_2CH_2SO_2CH=CH_2$ |
| | | R' = $-CONH_2C(CH_3)_2CH_2COCCH_3$ |
| P-4 | x = 92, y = 8, z = 0, | R = -⟨phenyl⟩-$SO_2CH_2CH_2SO_2CH=CH_2$ |
| P-5 | x = 92, y = 8, z = 0, | R = -⟨phenyl⟩-$CH_2SO_2CH_2CH_2Cl$ |
| P-6 | x = 92, y = 8, z = 0, | R = $CONHCH_2CH_2CH_2COON$ (succinimidyl) |
| P-7 | x = 92, y = 8, z = 0, | R = $-CONHCH_2NHCOCH_2CH_2SO_2CH_2CH_2Cl$ |
| P-8 | x = 80, y = 8, z = 12, | R = $-CONHCH_2NHCOCH_2CH_2SO_2CH_2CH_2Cl$ |
| | | R' = $-CONH_2C(CH_3)_2CH_2COCCH_3$ |
| P-9 | x = 80, y = 8, z = 12, | R = -⟨phenyl⟩-$CH_2SO_2CH=CH_2$ |
| | | R' = $-CONHCH_2OH$ |
| P-10 | x = 80, y = 8, z = 12, | R = -⟨phenyl⟩-$SO_2CH_2CH_2SO_2CH_2CH_2Cl$ |
| | | R' = $-CON$ (pyrrolidinyl) |
| P-11 | x = 80, y = 8, z = 12, | R = -⟨phenyl⟩-$CH_2SO_2CH_2CH_2Cl$ |
| | | R' = $-CON(CH_3)_2$ |
| P-12 | x = 92, y = 8, z = 0, | R = $-COOCH_2CH_2OCOCH_2SO_2CH=CH_2$ |

In the present invention, the acrylamide copolymer serves as a matrix component for supporting the medium for electrophoresis, and the acrylamide copolymer in the form of an aqueous gel can be prepared by Examples of the crosslinking agent containing the phenolic hydroxyl groups include hydroquinone, bisphenol A, and bisphenol sulfone.

Examples of the crosslinking agent containing the sulfinic acid groups include 1,4-butanedisulfinic acid and benzenedisulfinic acid.

Examples of the crosslinking agent containing the thiol groups include thioethanolamine and p-aminothiophenol.

Examples of the crosslinking agent containing a combination of the amino group and thiol group include cysthiamine.

The crosslinking agent is preferably employed in an amount enough to accomplish gelatin, for instance in 0.5–5 equivalents per one equivalent of the reactive group contained in the copolymer of the present invention.

Processes for the synthesis of the preferable copolymers represented by P-1, P-2, P-7 and P-8 are illustrated below.

SYNTHESIS EXAMPLE 5

Synthesis of copolymer of 2-[3-(vinylsulfonyl)propionyloxy]ethyl acrylate and acrylamide (corresponding to P-1)

In a reaction vessel, a mixture of 60 ml. of N,N-dimethylformamide, 14.5 g. of 2-[3-(2-chloroethylsulfonyl)propionyloxy]ethyl acrylate, and 32.6 g. of acrylamide was purged by nitrogen gas and heated to 60° C. To the heated mixture was added 0.40 g. of 2,2'-azobis(2,4-dimethylvaleronitrile) [CAS Registry No. 4419-11-8], and the resulting mixture was heated under stirring for 2 hours. Subsequently, 0.20 g. of 2,2'-azobis(2,4-dimethylvaleronitrile) was added to the mixture, and the resulting mixture was further heated under stirring for 2 hours. The mixture was then chilled to 5° C., and after addition of 12.g. of sodium carbonate and 4.9 g. of triethylamine, stirred for one hour. The mixture was then stirred at room temperature for 1 hour. This was introduced into a cellulose tube and subjected to dialysis for 2 days. The remaining solid was freeze-dried to give 43 g. of white polymer: yield 95%.

The vinylsulfonyl content of thus obtained polymer was $1.0 \times 10^{-3}$ eq./g.

SYNTHESIS EXAMPLE 6

Synthesis of copolymer of N-{[3-(vinylsulfonyl)propanamido]methyl}acrylamide and acrylamide (corresponding to P-2)

In a 200-ml. reaction vessel, 5.65 g. of the monomer of the synthesis example 2, 12.8 g. of acrylamide, and 80 ml. of 50% aqueous methanol were heated to 60° C. under stirring. To the resulting mixture was added 0.1 g. of 2,2'-azobis(2,4-dimethylvaleronitrile) and after 30 min. further added 0.1 of the same reagent. The mixture was then heated under stirring for 1 hour, and chilled with ice-water to approx. 10° C. To the chilled mixture was added a solution of 2.5 g. of triethylamine in 80 ml. of methanol, and the mixture was further stirred. The mixture was then added under stirring to 1 l. of acetone. The produced precipitate was collected by filtration to give 15.9 g. of the desired polymer: yield 90%.

The sulfonyl content of thus obtained polymer was $0.95 \times 10^{-3}$ eq./g.

SYNTHESIS EXAMPLE 7

Synthesis of copolymer of N-{[3-(2-chloroethylsulfonyl)propanamido]methyl}acrylamide and acrylamide (corresponding to P-7)

In a 500-ml. reaction vessel, 10.3 g. of the monomer of the synthesis example 2, 15.6 g. of acrylamide, and 160 ml. of 50% aqueous methanol were heated to 60° C. under stirring. To the resulting mixture was added 0.2 g. of 2,2'-azobis(2,4-dimethylvaleronitrile) and after 30 min. further added 0.2 g. of the same reagent. The mixture was then heated under stirring for 1 hour. This was introduced into a cellulose tube and subjected to dialysis for 2 days. The remaining solid was freeze-dried to give 23 g. of the desired white polymer: yield 90%.

The chlorosulfonyl content of thus obtained polymer was $1.0 \times 10^{-3}$ eq./g.

SYNTHESIS EXAMPLE 8

Synthesis of copolymer of N-{[3-(2-chloroethylsulfonyl)propanamido]methyl}acrylamide, acrylamide and N-(1,1-dimethyl-2-oxobutyl)acrylamide (corresponding to P-8)

In a 500-ml. reaction vessel, 10.3 g. of the monomer of the synthesis example 2, 29.2 g. of acrylamide, 11.3 g. of N-(1,1-dimethyl-2-oxobutyl)acrylamide, and 160 ml. of 50% aqueous methanol were heated to 60° C. under stirring. To the resulting mixture was added 0.2 g. of 2,2'-azobis(2,4-dimethylvaleronitrile) and after 30 min. further added 0.2 g. of the same reagent. The mixture was then heated under stirring for 1 hour. This was introduced into a cellulose tube and subjected to dialysis for 2 days. The remaining solid was freeze-dried to give 43.2 g. of the desired white polymer: yield 85%.

The chlorosulfonyl content of thus obtained polymer was $0.8 \times 10^{-3}$ eq/g.

The acrylamide copolymer preferably employable in the invention has a molecular weight in the range of approx. 10,000 to approx. 1,000,000. The viscosity of a solution for the formation of the medium for electrophoresis (referred to as gel-forming solution) can be controlled by selecting the molecular weight. The gel-forming solution can be casted or coated on a horizontally placed support in a conventional manner to form the medium for electrophoresis of the present invention.

The medium for electrophoresis (referred to as "polyacrylamide gel medium" or simply "gel medium") contains a modifier.

As the modifier, a compound containing at least one carbamoyl group can be used. Examples of the modifier include urea and formamide. Urea is most preferred. The modifier can be used in an amount of approx. 40 to 60 wt.% based on the volume of the aqueous gel containing the monomer and crosslinking agent. In the case that urea is used as the modifier, the amount generally ranges from approx. 6 moles (approx. 360 g.) per one liter of the aqueous gel containing the monomer and crosslinking agent to the saturation amount, preferably from approx. 7 moles (approx. 420 g.) to the saturation amount.

A pH buffer agent can be contained in the polyacrylamide gel medium of the invention. Any buffer agent which is able to buffer a solution to a range of pH 8.0 to 9.0, preferably pH 8.2 to 8.3 can be used. Buffer agents employable in the invention are described in publication such as "Chemistry Handbook, Fundamental Edition"

compiled by The Chemical Society of Japan (Maruzen Ltd., Tokyo, 1966) pages 1312–1320; "Modern Electrophoresis" editted by Aoki & Nagai (Hirokawa Shoten, 1973), pages 320–322; "Data for Biochemical Research" compiled by R. M. C. Dawson et al., second edition (Oxford at the Clarendon Press, 1969) pages 476–508; "Biochemistry" 5, 467 (1966); and "Analytical Biochemistry" 104, pages 300–310 (1966). Examples of the buffer agent include tris(hydroxymethyl)aminomethane (Tris), N,N-bis(2-hydroxyethyl)glycine (Bicine), N-2-hydroxyethylpiperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroymethy)methyl]-3-aminopropanesulfonic acid (TAPS) or its Na or K salt; as well as an acid, an alkali, and a salt employable in combination with these compounds. Preferable examples of the buffer agent include Tris, boric acid-EDTA.2Na (pH 8.2).

The polyacrylamide gel medium of the invention preferably contains a water-soluble polymer. As the water-soluble polymer, a water-soluble polymer of the addition polymerization type or condensation polymerization type can be used. Examples of the polymer of the addition polymerization type include non-ionic water-soluble polymers such as polyvinyl alcohol, polyvinyl pyrrolidone, and polyacrylamide. Examples of the polymer of the condensation polymerization type include non-ionic water-soluble polyalkylene glycols such as polyethylene glycol and polypropylene glycol. The water-soluble polymer of molecular weight ranging from approx. 10,000 to 1,000,000 is preferably used. Among these water-soluble polymers, polyacrylamide and polyethylene glycol are preferable. The water-soluble polymer is used in a range of approx. 2 to 100 wt.%, preferably, approx. 5 to 50 wt.%, based on the total weight of the monomer and crosslinking agent.

The addition of a water-soluble polymer serves to impart elasticity to the gel medium, and thus modified gel medium is still elastic even if it is dried. Thus, the gel medium is so improved as to be free from the brittleness, whereby the gel medium becomes hardly breakable. Further, the viscosity of the gel medium can be controlled by selecting the molecular weight and amount of the water-soluble polymer.

The polyacrylamide gel medium preferably contain agarose. There is no specific limitation on the agarose to be contained in the gel medium, and any type of agarose such as low-electroendosmosis agarose, medium-electroendosmosis agarose, or high-electroendosmosis agarose can be used. Examples of agarose employable in the invention include agaroses disclosed in Japanese Patent Provisional Publication Nos. 55(1980)-5730, 55(1980)-110946 (corresponding to U.S. Pat. No. 4,290,911 and GB No. 2 042 571A), 57(1982)-502098 (WO 82/02599, U.S. Pat. No. 4,319,976), etc. The amount of agarose to be added ranges from approx. 0.2 to 2 wt/v %, preferably from approx. 0.3 to 1.2 wt/v %, based on the volume of the aqueous gel containing the monomer and crosslinking agent. It becomes possible by the addition of agarose that the viscosity of the gel-forming solution can be controlled through changing the temperature of the solution; whereby suppressing flowability of the solution as well as facilitating the formation of the gel medium.

The polyacrylamide gel medium of the invention is formed by radical crosslinking polymerization between the monomer such as acrylamide with the bifunctional compound (crosslinking agent) in an aqueous medium in which the water-soluble polymer and agarose are dissolved almost homogeneously. The gel is assumed to have a structure in which the water-soluble polymer and agarose are dispersed in the three dimensional crosslinked polymer formed by the reaction of the monomer and cross-linking agent, and the water-soluble polymer and agarose dispersed and further entangle with the three dimensional crosslinked polymer structure.

The polyacrylamide gel medium of the invention may contain an oxidation inhibitor. The oxidation inhibitor can be chosen from various compounds heretofore known as oxidation inhibitors employable for the gel medium for electrophoresis. Examples of the oxidation inhibitor include 1,4-dithiothreitol and 2-mercaptoethanol.

A polyol compound such as glycerol or ethylene glycol can be contained in the polyacrylamide gel medium of the invention as a wetting agent. The polyol compound can be introduced in an amount of approx. 5 to 40 wt.% based on the volume of the aqueous gel medium. Glycerol is particularly preferable among the polyol compounds. The addition of the wetting agent serves to keep the gel medium from excessive dryness possibly caused by evaporation of water during storage of the medium, whereby preventing the medium from turning brittle or cracking caused by the excessive dryness. Thus, the improvement of physical properties of the gel medium is accomplished.

In the case that the polyacrylamide gel medium of the invention is employed in the form of a membrane or layer, it can be prepared by a process in which a gel-forming solution is coated by a known method on an electric insulation support having a smooth hydrophilic surface, and the gel-forming solution is crosslinked to polymerization thereon. Examples of the support include glass plate, hydrophilic polymers in the form of plate or sheet, and other polymers (e.g., polyethylene terephthalate, polycarbonate of bisphenol A, polyvinyl chloride, vinylidene chloride-vinyl chloride copolymer, polymethylmethacrylate, polyethylene, polypropylene, cellulose acetate, and cellulose acetate propionate) in the form of plate or sheet, a surface of which is made hydrophilic by a known surface treatment. Examples of the treatment employable to make the surface of these polymers hydrophilic include known methods such as irradiation with ultra-violet rays, glow discharge treatment, corona discharge treatment, flame treatment, electron beam treatment, chemical etching, or electrochemical etching. Nevertheless, the hydrophilic surface is not necessarily provided on the support, and the above-mentioned polymer sheet can be employed with no hydrophilic treatment.

In the case that the gel forming solution is crosslinked to polymerization on the surface of the support, the surface of the gel-forming solution can be covered with a cover film, sheet, or plate. The same material as employable for the support can be employed as the cover film, sheet, and plate. The cover film has generally thickness of 50 $\mu$m or less, preferably from approx. 3 $\mu$m to approx. 50 $\mu$m, specifically preferably from approx. 4 $\mu$m to approx. 40 $\mu$m.

The medium for electrophoresis of the present invention can be prepared in the same manner as employed in the conventional process for the preparation of a polyacrylamide gel medium except that no oxygen-free condition is required. Accordingly, the medium for electrophoresis of the invention can be easily prepared in a mass scale.

The present invention will be further described by the following examples, but the examples are by no means construed to restrict the invention.

EXAMPLE 1

The acrylamide copolymer gel-forming solution set forth in Table 1 was coated on a horizontally placed flat glass plate having a smooth surface under atmospheric conditions to produce thereon a membrane of approx. 40 μm thick. Then, the formed gel membrane was observed.

TABLE 1

| Composition of Gel Medium | | | | |
|---|---|---|---|---|
| | Sample No. | | | |
| | 1 | 2 | 3 | 4 |
| Gel-Forming Solution | | | | |
| Polymer | P-1 | P-2 | P-2 | P-8 |
| Urea | 42 g | 42 g | 42 g | 42 g |
| Tris(hydroxymethyl)-aminomethane | 1.08 g | 1.08 g | 1.08 g | 1.08 g |
| Boric Acid | 0.55 g | 0.55 g | 0.55 g | 0.55 g |
| EDTA.2Na | 93 mg | 93 mg | 93 mg | 93 mg |
| Water | (added to make 100 ml.) | | | |
| 1,3-Propanediamine | 530 mg | 530 mg | 880 mg | — |
| 1,3-Propanedithiol | — | — | — | 770 mg |

Remarks: The amount of each polymer was 11.86 g. A combination of tris(hydroxymethyl)aminomethane, boric acid and EDTA.2Na was a buffer composition (pH 8.2).

Each of the samples No. 1 to 4 (samples according to the present invention) was treated in atomospheric conditions in which oxygen was present to give a desired gel membrane.

Further, the comparison between the sample 2 and sample 3 containing the crosslinking agent (amine compound) in a greater amount than the sample 2 indicated that the sample 3 required shorter period for gelation than the sample 2. Accordingly, it was confirmed that the addition of a crosslinking agent in a greater amount was effective for shortening the period required for gelation.

It was further confirmed that a gel membrane in a similar quality was prepared by the use of a thiol compound in place of the amine compound.

Thus, it was concluded that the preparation of the medium for electrophoresis of the present invention required no oxygen-free conditions, and accordingly the procedure for the preparation was remarkably facilitated as compared with the conventional membrane.

COMPARISON EXAMPLE 1

Water was added to acrylamide (11.87 g.), N,N'-methylenebisacrylamide (0.63 g.), urea (42 g.), tris(hydroxymethyl)aminomethane (1.08 g.), boric acid (0.55 g.) and EDTA.2Na (93 mg.) to prepare 100 ml. of an aqueous solution. To the aqueous solution were added 1.3 ml. of aqueous ammonium peroxodisulfate solution (5 wt.%) and 33 μl of N,N,N',N'-tetramethylethylenediamine to prepare an acrylamide gel-forming solution. The gel-forming solution was coated with thickness of approx. 400 μm on a horizontally placed flat glass plate having smooth surface under atmospheric conditions. There was observed no formation of the desired gel membrane.

Other portion of the above gel-forming solution was introduced in a cell (space clearance 400 μm) prepared by means of a combination of two flat glass having smooth surface and a spacer plate of 400 μm thick. Then the gelation under oxygen-free condition was observed. The formation of the gel membrane was confirmed.

EXAMPLE 2

Four polyacrylamide gel mediums were prepared using the four gel-forming solutions identified in Example 1.

A sample ($^{32}$P-DNA cleaved by Maxam-Gilbert method) was electrophoresed on the gel mediums for sequencing the DNA. Satisfactory electrophoretic pattern was formed on the gel medium for every case. Thus, accurate DNA sequencing was accomplished.

The gel medium prepared from the conventional gel-forming solution (Comparison Example 1) was also employed for the same electrophoresis as above, and satisfactory pattern was formed.

We claim:

1. A medium for electrophoresis in the form of an aqueous gel comprising an acrylamide copolymer having at least one constitutional repeating unit selected from the group consisting of:

(1) a repeating unit having the formula (1):

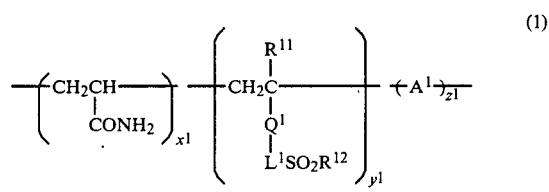

in which $R^{11}$ is the hydrogen atom or an alkyl group containing 1–6 carbon atoms; $Q^1$ is —COO—, —CON($R^{11}$)—, or an arylene group containing 6–10 carbon atoms; $L^1$ is a divalent group containing at least one linkage selected from the group consisting of —COO— and —CON($R^{11}$)— and containing 3–15 carbon atoms, or a divalent group containing at least one linkage selected from the group consisting of —O—, —N($R^{11}$)—, —CO—, —SO—, —SO$_2$—, —SO$_3$—, —SO$_2$N($R^{11}$)—, —N($R^{11}$)CON($R^{11}$)— and —N($R^{11}$)COO—, and containing 1–12 carbon atoms, in which $R^{11}$ has the same meaning as defined above; $R^{12}$ is —CH=CH$_2$ or —CH$_2$CH$_2$X$^1$, in which X$^1$ is a substituent replaceable with a nucleophilic group or releasable in the form of HX$^1$ by a base; A$^1$ is a divalent group derived from an ethylenic unsaturated monomer copolymerizable with monomers forming over unit portions; and $x^1$ and $y^1$ both representing molar percents range from 50 to 99, and from 1 to 50, respectively, and $z^1$ represents the remaining molar percent including 0;

(2) a repeating unit having the formula (2):

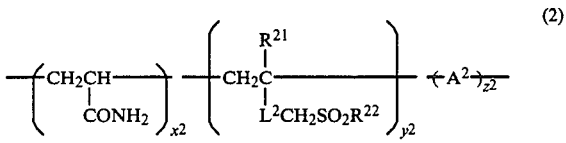

in which $R^{21}$ is the hydrogen atom or an alkyl group containing 1–6 carbon atoms; $R^{22}$ is —CH=CH$_2$ or —CH$_2$CH$_2$X$^2$, in which X$^2$ is a substituent replaceable with a nucleophilic group or releasable in the form of $HX^2$ by a base; $L^2$ is a divalent group selected from the group consisting of an alkylene group containing 1–6 carbon atoms, an arylene group containing 6–12 carbon atoms, $-COZ^2-$, and $-COZ^2R^{23}-$, in which $R^{23}$ is an alkylene group containing 1–6 carbon atoms, or an arylene group containing 6–12 carbon atoms, and $Z^2$ is the oxygen atom or NH; $A^2$ is a divalent group derived from an ethylenic unsaturated monomer copolymerizable with monomers forming other unit portions; and $x^2$ and $y^2$ both representing molar percents range from 50 to 99, and from 1 to 50, respectively, and $z^2$ represents the remaining molar percent including 0; and (3) a repeating unit having the formula (3):

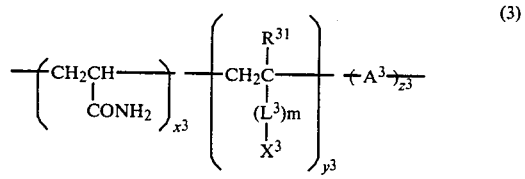

in which $R^{31}$ is the hydrogen atom or an alkyl group containing 1–6 carbon atoms; $L^3$ is a divalent linkage group containing 1–20 carbon atoms; $X^3$ is an active ester; $A^3$ is a divalent group derived from an ethylenic unsaturated monomer copolymerizable with monomers forming other unit portions; $x^3$ and $y^3$ both representing molar percents range from 50 to 99, and from 1 to 50, respectively, and $z^3$ represents the remaining molar percent including 0; and m is 0 or 1; and a water-soluble polymer selected from the group consisting of polyvinyl alcohol, polyvinyl pyrrolidone, polyacrylamide and polyalkylene glycols; agarose; and a modifier selected from the group consisting of urea and formamide.

2. The medium as claimed in claim 1 in which said acrylamide copolymer is crosslinked via a crosslinking agent containing in one molecule at least two nucleophilic groups selected from the group consisting of amino groups, phenolic hydroxyl groups, sulfinic groups, thiol groups, and a combination of amino and thiol groups.

3. The medium for electrophoresis as claimed in claim 1 in which said water-soluble polymer is contained in an amount of 2 to 100 wt.% based on the polyacrylamide solid amount and said agarose is contained in the aqueous polyacrylamide gel medium in an amount of 0.2 to 2 wt/v %.

4. The medium as claimed in any one of claim 1, 2 or 3, in which said acrylamide copolymer has the repeating unit of the formula (1).

5. The medium as claimed in any one of claims 1, 2 or 3, in which said acrylamide copolymer has the repeating unit of the formula (2).

6. The medium as claimed in any one of claims 1, 2 or 3, in which said acrylamide copolymer has the repeating unit of the formula (3).

* * * * *